United States Patent
Singh

(10) Patent No.: US 7,754,767 B2
(45) Date of Patent: Jul. 13, 2010

(54) METHOD FOR TREATMENT OF PREMATURE EJACULATION IN HUMANS

(75) Inventor: Chandra U. Singh, San Antonio, TX (US)

(73) Assignee: Trinity Laboratories, Inc., San Antonio, TX (US)

(*) Notice: Subject to any disclaimer, the term of this patent is extended or adjusted under 35 U.S.C. 154(b) by 1873 days.

(21) Appl. No.: 10/482,629

(22) PCT Filed: Nov. 6, 2003

(86) PCT No.: PCT/US03/35306

§ 371 (c)(1), (2), (4) Date: Dec. 24, 2003

(87) PCT Pub. No.: WO2004/043365

PCT Pub. Date: May 27, 2004

(65) Prior Publication Data

US 2004/0235954 A1    Nov. 25, 2004

Related U.S. Application Data

(60) Provisional application No. 60/424,229, filed on Nov. 6, 2002.

(51) Int. Cl.
- A01N 37/10 (2006.01)
- A01N 43/54 (2006.01)
- A01N 43/42 (2006.01)
- A01N 43/38 (2006.01)
- A01N 37/36 (2006.01)
- C07D 239/42 (2006.01)
- A61K 31/40 (2006.01)
- A61K 31/00 (2006.01)

(52) U.S. Cl. .......... 514/569; 514/256; 514/210.21; 514/410; 514/289; 514/159; 514/420; 514/570

(58) Field of Classification Search .......... 514/569, 514/256, 210.21, 289, 159, 420, 570, 410
See application file for complete search history.

(56) References Cited

U.S. PATENT DOCUMENTS

| | | | | |
|---|---|---|---|---|
| 5,863,927 A * | 1/1999 | Smith et al. | ................ | 514/289 |
| 6,403,597 B1 * | 6/2002 | Wilson et al. | ................ | 514/256 |
| 2002/0037828 A1 * | 3/2002 | Wilson et al. | ................ | 514/1 |
| 2002/0091129 A1 * | 7/2002 | Boolell | ................ | 514/252.16 |
| 2002/0132857 A1 * | 9/2002 | Bar-Or | ................ | 514/649 |
| 2003/0186872 A1 * | 10/2003 | Chang et al. | ................ | 514/12 |
| 2005/0203125 A1 * | 9/2005 | Yakatan et al. | ................ | 514/305 |
| 2006/0094704 A1 * | 5/2006 | Boolell | ................ | 514/210.21 |
| 2008/0153841 A1 * | 6/2008 | Boolell | ................ | 514/252.16 |

OTHER PUBLICATIONS

Mitchell et al. (Proc Natl Acad Sci 90, 11693-97, 1994).*
Mandell et al. (J Clin Pharamacol. Jun. 1995 3596), 588-93) Abstract only.*
Oshman and Mirisola document (http://www.oshmanlaw.com/pharmaceutical_litigation/quinine.asp).*
Dextromethorphan (http://www.drugs.com/dextromethorphan.html?printable=1.*
Abdel-Hamid et al (Intl. J of Impotence Research, Jan. 2001, 13, 41-45).*
Jetter, Clin Pharmaol Ther 2002, 71(1), 21-9), Abstract.*
"Phosphodieseterase-5 inhibitors for Erectile Dysfunction", p. 1-4.*

* cited by examiner

Primary Examiner—Sreeni Padmanabhan
Assistant Examiner—Umamaheswari Ramachandran
(74) Attorney, Agent, or Firm—Nanda P.B.A. Kumar; Reed Smith LLP

(57) ABSTRACT

The present invention belongs to the fields of pharmacology, medicine and medicinal chemistry, and provides methods and compositions for treating sexual dysfunction; more particularly, the invention relates to treatment of premature ejaculation in humans.

9 Claims, 3 Drawing Sheets

METHOD FOR TREATMENT OF PREMATURE EJACULATION IN HUMANS

This regular utility patent application claims priority to U.S. Provisional Patent Application Ser. No. 60/424,229, filed Nov. 6, 2002, and is incorporated herein by reference for all purposes.

BACKGROUND OF THE INVENTION

Primitive premature ejaculation is regarded as the most common sexual disorder of the male. This may cause a loss of the ability to achieve sexual accommodation which is necessary for the satisfaction of the human instinctive desire. Recently, it has been determined that the number of cases manifesting various symptoms caused by such loss of sexual accommodation is rather large. The sexual problems due to premature ejaculation in men lead to social difficulties, such as asthenia due to the loss of self-confidence, as well as domestic discord. Premature ejaculation is defined as persistent or recurrent ejaculation before, upon, or shortly after penetration By nature, a woman is so evolved that she experiences the sex act markedly less intensely than a man, at least at the commencement of sexual activity. She must, therefore, have more time in order to reach the orgasm which provides natural relaxation of the whole nervous system strained to the maximum during the act. To this day the sense of touch plays an important role in human sex life; particularly sensitive to touch are the erogenous zones, first and foremost among them being the areas where skin borders on mucous membrane as, for example, in the vicinity of the oral cavity, the rectum, female genitals and breast nipples. The erogenous zone of a woman can be her entire body surface. In such cases it is possible to evoke lascivious feelings in her by touching any part of her body. But it is most often the case that erogenous zones are localized in strictly defined places such as: the clitoris, labia minora and the vagina. There are, additionally, many such sensitive points apart from the sex organs. These are: the lips, the ears, eyelids, neck, nipples, etc. In some cases these points are so sensitive that merely touching them can produce an orgasm in a woman.

However in the case of men, the erogenous zones are confined solely to the genitals and adjacent areas. It is not surprising, therefore, that an experienced male partner is sometimes obliged to undertake veritable journeys of exploration, in his search for these points, without which no one can activate the complex apparatus of female sexual reflexes. That is one reason the male often needs incomparably less time in order to reach orgasm—which usually concludes the sex act not only for himself but also for his partner. At the commencement of the sex act the man already finds himself at a certain level of excitement, which is essential to erection and without which this act becomes quite impossible. He is unable to continue the act out of consideration for his partner because immediately after orgasm and the associated ejaculation detumescence takes place and all further frictiones in vagina are impossible.

The ideal intercourse would be one in which, following immersing the penis into the vagina, both parties reached the boundary of orgasm simultaneously and, having crossed it, ended the sex act together (FIG. 1). This happens sometimes where a woman experienced in sexual intercourse can compensate for the excitement missing at the beginning of the act and reach the finishing line together with her partner in spite of that. For young and middle-aged men the norm of normal ejaculation vacillates between 2-6 minutes after the immersing the penis into the vagina.

The premature ejaculation occurs very frequently in the modern human sexual act. It concerns the fact that shortly after immersing the penis into the vagina takes place (FIG. 2), sometimes after 2-3 movements, ejaculation and orgasm occur; the erection vanishes and the sex act is ended. Obviously in such a situation the woman is only aroused, while there can be no question of release. Obviously there can be no question of sexual satisfaction and normal relaxation of the female partner in the presence of any kind of male impotence, whether through inadequate erection or through premature ejaculation.

Erection of the penis may be a self-perpetuating process of three steps: 1) vasodilation; 2) release of endogenous smooth-muscle relaxants; and, 3) progression of these effects distal from the initial site of onset. This has been termed the "cascade effect". Papaverine is an opium alkaloid and works as a smooth muscle relaxer possibly by cyclic GMP phosphodiesterase inhibition. It relaxes the musculature of the vascular system of the penis and increases blood flow (Papaverine Topical Gel Treatment For Erectile Dysfunction, Urology, Vol. 133(2)(1995), pp. 361-365). Another compound found useful in the treatment of impotence is prostaglandin E1, a naturally occurring compound that acts to increase arterial inflow to the penis and may also restrict venous outflow. Prostaglandin E1 is preferred to other compounds used in injections for the treatment of impotence because it is metabolized locally in the penis and is less likely to cause systemic symptoms such as hypotension. As a modified vascular tissue, corpora carvernosa of the penis (ccp) produces and secretes the same range of autocrine and paracrine regulators as conventional vascular tissue. The smooth muscle tone of the ccp, however, does not appear to be regulated in the same manner as in the vascular wall. Presently it is postulated that the tone or contractility of ccp is modulated by adrenergic regulation and locally produced NO and endothelin. In the ccp, most studies have been directed to observing the relaxing effects of NO, vasoactive intestinal peptide (VIP), calcitonin gene-related peptide (CGRP) and parasympathetic innervation, which also have similar effects on conventional and ccp vascular smooth muscle.

During normal penile erections, when the inflow of blood to the ccp engages the sinusoidal spaces, the trabecular tissue compresses small carvernosal veins against the thick fibrous tissue surrounding the corpora to maintain the erection. To mediate these changes in blood flow, nitric oxide is released from postsynaptic parasympathetic neurons and, to a lesser extent, endothelial cells and α-adrenergic neurons are inhibited in the arterial and trabecular smooth muscle. Nitric oxide, which is readily diffusible, stimulates the formation of increased cyclic guanosine monophosphate (GMP) in the corpus carvernosum by guanylate cyclase to relax the smooth muscle cells.

Recently, the oral use of the citrate salt of sildenafil has been approved by the U.S. Food and Drug Administration (FDA) for the treatment of male erectile dysfunction. Sildenafil is reported to be a selective inhibitor of cyclic-GMP-specific phosphodiesterase type 5 (PDE5), the predominant isozyme metabolizing cyclic GMP formed in the corpus carvernosum. Since sildenafil is a potent inhibitor of PDE5 in the corpus carvernosum, it is believed to enhance the effect of nitric oxide, thereby increasing carvernosal blood flow in the penis, especially with sexual stimulation. Inasmuch as sildenafil at the currently recommended doses of 25-100 mg has little effect in the absence of sexual stimulation, sildenafil is believed to restore the natural erectile response to sexual stimulation but not cause erections in the absence of such stimulation (Goldstein 1998). The localized mechanism by which cyclic GMP stimulates relaxation of the smooth muscles has not been elucidated.

Normal ejaculatory function in the human male implies a coordinated sequence of smooth and striate muscular contractions to promote projectile, antegrade transport of seminal fluid. This process begins with transmission of afferent nerve stimuli via the internal pudendal nerve from the penile shaft to higher centers. To complete the ejaculatory reflex efferent stimuli are transmitted from the anterolateral columns of the spinal cord and emerging from the thoracolumbar level to comprise a hypogastric or sympathetic plexus. From the interior mesenteric ganglion short adrenergic postganglionic fibers terminate in the seminal vesicles, vasal ampullae, and bladder neck. Sympathetic innervation of the seminal vesicles results in seminal emission into the posterior urethra. Appropriately timed bladder neck closure prevents retrograde passage of this semen bolus, which is propelled in the antegrade direction by clonic contracts of the bulbocarvernosus and ischiocarvernosus muscles of the pelvic floor. Ejaculation is a centrally, integrated peripheral evoked reflex, which occurs as a result of $\alpha 1$-adrenergic receptor activation. Effective pharmacological drugs for the treatment of premature ejaculation exist, but they suffer from severe side effects, for example clomipramine and phenoxybenzamine. Other treatments have a limited effectiveness (metoclopramide and the like).

PGE2, PGF2$\alpha$, PGF2$\beta$, PGA2, and PGB2, and their esters and pharmacologically acceptable salts, are extemely potent in causing various biological responses. For that reason, these compounds are useful for pharmacological purposes. See, for example, Bergstrom et al., Pharmacol. Rev. 20, 1 (168), and references cited therein. A few of those biological responses are systemic arterial blood pressure lowering in the case of PGE2, PGF2$\beta$, and PGA2 as measured, for example, in anesthetized (pentobarbital sodium) pentolinium-treated rats with indwelling aortic and right heart cannulas; pressor activity, similarly measured, for PGF2$\alpha$; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of PGE2 and PGA2 as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of PGE2 and PGB2, stimulation of epidermal proliferation and keratinization as shown when applied in culture to embryonic chick and rat skin segments. PGE2 is extremely potent in causing stimulation of smooth muscle, and is also highly active in potentiating other known smooth muscle stimulators, for example, oxytocic agents, e.g., oxytocin, and the various ergot alkaloids including derivatives and analogs thereof. Therefore PGE2 is useful in place of or in combination with less than usual amounts of these known smooth muscle stimulators, for example, to relieve the symptoms of paralytic ileus, to control or prevent atonic uterine bleeding after abortion or delivery, to aid in expulsion of the placenta, and during the puerperium.

A synthetic form of prostaglandin E1, alprostadil USP (alprostadil), is a long-chain carboxylic acid with vasodilatory effects. Alprostadil acts to increase arterial inflow to the penis. In vitro studies have shown that alprostadil causes a dose-dependent smooth muscle relaxation in isolated corpus carvernosum and corpus spongiosum preparations. When used in vivo, it is thought that intraurethral alprostadil is absorbed from the urethra, transported throughout the erectile bodies of the penis by way of communicating vessels between the corpus spongiosum and corpus carvernosum, and induces vasodilation of the targeted vascular beds. U.S. Pat. No. 5,658,936 teaches that similar to the vascular tissue, the corpus carvernosum penis produces and secretes angiotensin II, that plays an important role in modulation of the penile blood flow. Local, intracarvernosal, or systemic administration of angiotensin II antagonists or ACE inhibitors has a powerful effect on the penile blood flow. (U.S. Pat. No. 5,658,936: Enhancement of erectile function with renin-angiotensin system inhibitors)

Dextromethorphan (frequently abbreviated as DM) is the common name for(+)-3-methoxy-N-methylmorphinan (FIG. 3). It widely used as a cough syrup, and is described in references such as Rodd 1960 (full citations to articles are provided below) and Goodman and Gilman's Pharmacological Basis of Therapeutics. Briefly, DM is a non-addictive opioid comprising a dextrorotatory enantiomer (mirror image) of the morphinan ring structure which forms the molecular core of most opiates. DM acts at a class of neuronal receptors known as sigma receptors. These are often referred to as sigma opiate receptors, but there is some question as to whether they are opiate receptors, so many researchers refer to them simply as sigma receptors, or as high-affinity dextromethorphan receptors. They are inhibitory receptors, which means that their activation by DM or other sigma agonists causes the suppression of certain types of nerve signals. Dextromethorphan also acts at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors. Since NMDA receptors are excitatory receptors, the activity of DM as an NMDA antagonist also leads to the suppression of certain types of nerve signals, which may also be involved in some types of coughing. Due to its activity as an NMDA antagonist, DM and one of its metabolites, dextrorphan, are being actively evaluated as possible treatments for certain types of excitotoxic brain damage caused by ischemia (low blood flow) and hypoxia (inadequate oxygen supply), which are caused by events such as stroke, cardiac arrest, and asphyxia. The anti-excitotoxic activity of dextromethorphan and dextrorphan, and the blockade of NMDA receptors by these drugs, are discussed in items such as Choi 1987, Wong et al 1988, Steinberg et al 1988, and U.S. Pat. No. 4,806,543 (Choi 1989). Dextromethorphan has also been reported to suppress activity at neuronpal calcium channels (Carpenter et al 1988). Dextromethorphan and the receptors it interacts with are further discussed in Tortella et al 1989, Leander 1989, Koyuncuoglu & Saydam 1990, Ferkany et al 1988, George et al 1988, Prince & Feeser 1988, Feeser et al 1988, Craviso and Musacchio 1983, and Musacchio et al 1988.

DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation; in this process, one of the two pendant methyl groups is replaced by hydrogen. If the second methyl group is removed, the resulting metabolite is called 5-hydroxymorphinan. Dextrorphan and 5-hydroxymorphinan are covalently bonded to other compounds in the liver (primarily glucuronic acid or sulfur-containing compounds such as glutathione) to form glucuronide or sulfate conjugates which are eliminated fairly quickly from the body via urine bloodstream. This enzyme is usually referred to as debrisoquin hydroxylase, since it was discovered a number of years ago to carry out a hydroxylation reaction on debrisoquin. It is also referred to in various articles as P450 DB or P450-2D6. It apparently is identical to an enzyme called sparteine monooxygenase, which was shown years ago to metabolize sparteine; it was not until recently that scientists realized that a single isozyme appears to be primarily responsible for oxidizing both debrisoquin and sparteine, as well as dextromethorphan and various other substrates. Debrisoquin hydroxylase belongs to a family of enzymes known as "cytochrome P-450" enzymes, or as "cytochrome oxidase" enzymes. Monooxygenation of chemical materials has been ascribed to cytochromes P450 (P450). These hemoprotein containing monooxygenase enzymes displaying a reduced carbon monoxide absorption spectrum maximum near 450 nm have been shown to catalyze a variety of oxidation reactions including hydroxylation of endogenous and exogenous compounds (Jachau, 1990). An extensive amount of research has been conducted on the mechanism's by which P450's can catalyze oxygen transfer reactions (Testa and Jenner, 1981; Guengerich, 1992; Brosen et al, 1990; Murray et al, 1990; and Porter et al, 1991).

The P450 reaction cycle proceeds briefly as follows: initial binding of a substrate molecule (RH) to the ferric form of the cytochrome results in the formation of a binary complex and a shift in the spin equilibrium of the ferric enzyme from the low- to high-spin state. Some evidence has been presented that suggests this configuration more readily accepts an electron from the flavoprotein reductase to form the ferrous P450-substrate complex. However, not all P450s exhibit a relationship between high-spin content and reduction rate. Indeed, it has been proposed that several factors, including the nature of the P450 substrate, the topography of the enzyme/substrate complex, and the potentials of oxidizable atoms each play a role in regulation of the reduction rate. Molecular oxygen binds to the ferrous P450-substrate complex to form the ferrous dioxygen complex which is then reduced by a second electron from the P450 reductase (or perhaps, in some cases, from reduced nicotinamide adenine dinucleotide via cytochrome b5 and its reductase). Dioxygen bond cleavage in the reduced ferrous dioxygen complex results in the insertion of one atom of oxygen into the substrate, reduction of the other oxygen atom to water, and restoration of the ferric hemoprotein.

Individual members of the P450 family of enzymes and associated mixed function oxidase activities have been described in extrahepatic tissues including brain, adrenal, kidney, testis, ovary, lung and skin. Individual P450s have likewise been characterized in terms of their inducibility by selected chemical classes. Induction of specific P450 enzymes, such as the P450 1A1 and 1A2 subfamily have been extensively studied with respect to regulatory processes of increased mRNA transcription and expression of enzymatic activity. It has been ascertained that materials such as beta-naphthaflavone (beta-NF), 3-methylcholanthrene (3-MC), arochlor 1254 (ACLR) and 2,3,7,8-tetrachlorodibenzo-p-dioxin (TCDD) are materials that have been categorized as inducers of P450 enzymes bearing the designated P450 1A subfamily (Murray et al, 1990; and Guengerich, 1989).

A number of compounds inhibit the activity of the debrisoquin hydroxylase (sparteine monooxygenase) isozyme (Inaba et al 1985). The most powerful of these inhibitors is quinidine (FIG. 3), a dextrorotatory stereoisomer of quinine; it is normally used to treat cardiac arrhythmias. Inaba et al (1986) and Nielsen et al (1990) discuss the ability of quinidine to inhibit the oxidation of sparteine in in vivo animal tests, and Brinn et al (1986), Brosen et al (1987), and Broly et al (1989) discuss the ability of quinidine to inhibit DM metabolism in liver cell preparations. In addition to the inhibition of debrisoquin hydroxylase, which is exceptionally potent and easily demonstrated, other cytochrome P450 isozymes are also likely to be suppressed by quinidine, with varying levels of binding affinity. Accordingly, even though quinidine exerts its most marked effect on debrisoquin hydroxylase, it is likely to suppress a number of other cytochrome P450 enzymes as well, thereby subjecting a patient to a more general loss of normal and desirable liver activity. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. It has been shown that the administration of a compound which inhibits debrisoquin hydroxylase, in conjunction with DM, causes a major increase in the concentration and stability of DM in the blood of patients, compared to patients who receive only DM; and the administration of a debrisoquin hydroxylase inhibitor in conjunction with DM has a clear and substantial impact on the detectable effects of DM in humans.

Non-steroidal anti-inflammatory drugs (NSAIDs) are widely used for treating common inflammation. NSAIDs mainly inhibit the synthesis of prostaglandins in the human body by inhibiting the enzyme cyclo-oxygenase(COX) which is essential for the synthesis of prostaglandins. The enzyme COX has two isomers called COX-1 and COX-2. COX also known as prostaglandin H synthase, is an enzyme implicated in the mediation of pain, fever, and inflammation. It catalyzes the oxidative conversion of arachidonic acid into prostaglandin H2, a key intermediate in the biosynthetic pathway of prostaglandins, prostacyclins, and thromboxanes, which in turn mediate a variety of physiological effects both beneficial and pathological. Recently, it was discovered that two COX isoforms exists: COX-1, expressed constitutively in many tissues, and COX-2, an induced isoform having elevated expression in inflamed tissues. COX-1 is thought to be involved in ongoing housekeeping functions, for example gastric cytoprotection, while COX-2 is the isoform implicated in the pathological effects mentioned above. Nonsteroidal anti-inflammatory agents (NSAIDs) such as aspirin, ibuprofen and indomethacin inhibit both COX-1 and COX-2. COX-2 inhibitors, celecoxib (Celebrex) and rofecoxib (Vioxx), are recently introduced prescription NSAIDs for osteoarthritis. Unlike previously available NSAIDs, which inhibit cyclooxygenase-1 (COX-1) and COX-2, celecoxib and rofecoxib specifically (about 350 fold) inhibit cyclooxygenase-2 (COX-2). Both actions are beneficial in blocking production of prostaglandins. However, inhibition of COX-1 is responsible for some side effects of older NSAIDs, such as upper gastrointestinal irritations and inhibition of platelet aggregation. Because celecoxib and rofecoxib specifically target COX-2, they do not affect platelet aggregation and are less likely to produce stomach and upper intestinal irritations.

At present, the treatment of choice for premature ejaculation is psychotherapy, either as a behavioural dual team sex therapy according to Master & Johnson protocol, or individual psychotherapy (Rifelli and Moro. Sessuologia Clinica.

Bologna, 1989). Previous methods of treating premature ejaculation include psychological therapies, topical anesthetics and the use of devices (U.S. Pat. Nos. 5,535,758, 5,063,915, 5,327,910, and 5,468,212). All of these methods may have significant drawbacks. Psychological therapies benefit only a subset of patients and require specialized therapists who may not be available to all patients, particularly in remote areas. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous, and reveal the very condition which the suffering partner may prefer to conceal. Additionally, devices can cause irritation to one or both partners.

Methods for treating premature ejaculation by systemic administration of several different antidepressant compounds have been described (U.S. Pat. Nos. 4,507,323, 4,940,731, 5,151,448, and 5,276,042; PCT Publication No. WO95/13072). However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation. Additionally, the stigma of mental illness associated with antidepressant therapy can discourage patients from beginning or continuing such treatments. Administration of the antidepressant fluoxetine has been claimed to treat premature ejaculation (U.S. Pat. No. 5,151,448). However, the administration of fluoxetine may have many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, side effects of oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis, and skin rashes. Fluoxetine interacts with a range of drugs, often by impairing their metabolism by the liver.

U.S. Pat. No. 4,940,731 describes the oral or parenteral administration of sertraline for treating premature ejaculation. It has been recognized that sertraline shares many of the same problems as fluoxetine; (see Martindale, The Extra Pharmacopoeia, 31st edition, at p. 333 (London: The Royal Pharmaceutical Society, 1996)). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity, leading to memory changes, confusion, irritability, chills, pyrexia and muscle rigidity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy. U.S. Pat. No. 5,276,042 describes the administration of paroxetine for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia. Thus there is a need for a method of treating premature ejaculation that requires no specialized psychological therapy, can be used conveniently and without embarrassment, and does not involve the problems associated with prior therapeutic methods.

U.S. Pat. No. 6,037,360 discloses that administration of various serotonin agonists and antagonists is effective in the treatment of premature ejaculation. The adverse effects occurring most frequently during treatment with serotonin inhibitors are gastrointestinal disturbances, such as, for example nausea, diarrhea/loose stools, constipation. (Drugs 43 (Suppl. 2), 1992). Nausea is the main adverse effect in terms of incidence. Moreover it has been frequently observed that after administration of serotonin inhibitors, patients suffer from dyspepsia.

U.S. Pat. No. 5,707,999 teaches that two specific α1-blockers, alfuzosine and terazosine, are effective in the treatment of psychogenic premature ejaculation and said drugs turned out to be effective in patients who proved to have no benefit from psychological therapy. However terazosine and its analogs have several side effects including headache, nausea, weight gain, dizziness, somnolence, dyspnea and blurred vision.

SUMMARY OF THE INVENTION

Applicant has now developed compositions, (combinations and formulations) which are administered to a human in the treatment of premature ejaculation. These compositions, (combinations and formulations) employ, combine, or incorporate (as the case may be) a plurality of effective non-toxic dosage amounts, each dosage amount comprising an effective non-toxic dosage amount of a drug, for example, a drug which inhibits prostaglandin synthesis, for example, an NSAID and an effective non-toxic dosage amount of a form of Dextromethorphan (preferably Dextromethorphan Hydrate or salt there of) and optionally, an effective non-toxic dosage amount of a cytochrome-P450 inhibitor, for example, quinidine (preferably quinidine hydrate or salt there of).

Applicant has also developed compositions, (combinations and formulations) which are administered to a human in the treatment of premature ejaculation and erection. These compositions, (combinations and formulations) employ, combine, or incorporate (as the case may be) a plurality of effective non-toxic dosage amounts, each dosage amount comprising an effective non-toxic dosage amount of a drug which inhibits cyclic-GMP-specific phosphodiesterase type 5 (PDE5), for example, sildenafil and an effective non-toxic dosage amount of a form of Dextromethorphan (preferably Dextromethorphan Hydrate or salt there of) and optionally, an effective non-toxic dosage amount of a cytochrome-P450 inhibitor, for example, quinidine (preferably quinidine hydrate or salt there of).

Accordingly, one object of the subject invention is to disclose that a combination of a non-steroidal anti-inflammatory substances or drugs (hereinafter referred to by the abbreviation NSAIDs) which involve in the prostaglandin biochemical pathways such as Ibuprofen, sodium salicylate, BW755c, BF389, naproxen, aspirin, acetaminophen, flurbiprofen, piroxicam, celecoxib, diclofenac, etodolac, fenoprofen, indomethacin, ketoprofan, ketoralac, oxaprocin, nabumetone, sulindac, tolmetin, rofecoxib, meclofenamate, oxaprozin, in humans, dextromethorphan which involves in anti-excitotoxic activity in humans and optionally a cytochrome P450 inhibitor such as quinidine, is very effective in delaying the onset of ejaculation in male humans.

According to yet another aspect of the invention, applicant has provided pharmaceutical compositions (combinations and formulations) comprising a plurality of dosage amounts each comprising, together with pharmaceutical excipients suitable for oral or parenteral adminstration, a therapeutically effective (to treat and to assist to resolve diseases and conditions of premature ejaculation in human male non-toxic (to the patient) dosage amount of a drug for example which inhibits prostaglandin synthesis, preferably being a non-steroidal anti-inflammatory drug (NSAID) which inhibits the synthesis of prostaglandins, for example, Ibuprofen, sodium salicylate, BW755c, BF389, naproxen, aspirin, acetaminophen, flurbiprofen, piroxicam, celecoxib, diclofenac, etodolac, fenoprofen, indomethacin, ketoprofan, ketoralac, oxaprocin, nabumetone, sulindac, tolmetin, rofecoxib, meclofenamate, oxaprozin, celecoxib, rofecoxib and an effective non-toxic dosage amount dosage amount of a form of Dextromethorphan and/or salts thereof (for example the hydrobromide salt) and/or homologues, analogues, derivatives, complexes, prodrugs, esters, fragments, and optionally an effective non-toxic dosage amount of a cytochrome-P450 inhibitor, for example, quinidine (preferably quinidine hydrate or salt there of).

It is another object of the invention to provide such a method wherein the pharmacologically active agent is administered orally. It is a further object of the invention to provide such a method wherein the pharmacologically active agent is administered parenterally.

In another object of the present invention, a method is provided for treating premature ejaculation, the method comprising administering to an individual in need of such treatment a pharmaceutical formulation containing an anti-inflammatory agent, dextromethorphan and optionally an agent which inhibits the oxidative activity of cytochrome-P450, such as a naphthyridine, xanthine, phenoxy amino alkane, carbamoyl imidazole, guanidine imidazole, e.g. cimetidine (N-cyano-N'-methyl-N"-[2[[(5-methyl-1H-imidazol-4 yl)methyl]thio]ethyl]guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime. Administration of the pharmaceutical formulation is carried out within the context of a predetermined dosing regimen such that the agent is effective in the treatment of premature ejaculation. Drug delivery may be accomplished through any route effective to provide relief from premature ejaculation, including oral, parenteral, buccal, rectal, topical, transdermal, transurethral, and intracarvernosal injection.

In another aspect of the invention, a pharmaceutical formulation is provided for carrying out the method of the invention. The pharmaceutical formulation comprises an effective amount of a selected anti-inflammatory agent, dextromethorphan, optionally, a cytochrome-P450 inhibitor, a pharmacologically acceptable carrier or vehicle, and, optionally (i.e., in topical, transdermal or transurethral formulations), an enhancer. Other types of components may be incorporated into the formulation as well, e.g., excipients, surfactants, preservatives (e.g., antioxidants), stabilizers, enzyme inhibitors, chelating agents, and the like, as will be appreciated by those skilled in the art of pharmaceutical formulation preparation and drug delivery.

Yet another object of the subject invention is to disclose that a combination of cyclic-GMP-specific phosphodiesterase type 5 (PDE5) inhibitors such as sildenafil which facilitates the erection of the penis in humans under sexual stimulation, dextromethorphan which involves in anti-excitotoxic activity in humans and optionally a cytochrome P450 inhibitor such as quinidine, is very effective in delaying the onset of ejaculation in male humans who have erection as well as ejaculation problems.

Thus, according to yet another aspect of the invention, applicant has provided pharmaceutical compositions (combinations and formulations) comprising a plurality of dosage amounts each comprising, together with pharmaceutical excipients suitable for oral or parenteral adminstration, a therapeutically effective (to treat and to assist to resolve diseases and conditions of premature ejaculation in human male non-toxic (to the patient) dosage amount of a drug for example which inhibits cyclic-GMP-specific phosphodiesterase type 5 (PDE5), for example, sildenafil and an effective non-toxic dosage amount dosage amount of a form of Dextromethorphan and/or salts thereof (for example the hydrobromide salt) and/or homologues, analogues, derivatives, complexes, prodrugs, esters, fragments, and optionally an effective non-toxic dosage amount of a cytochrome-P450 inhibitor, for example, quinidine (preferably quinidine hydrate or salt there of).

Yet in another object of the present invention, a method is provided for treating premature ejaculation, the method comprising administering to an individual in need of such treatment a pharmaceutical formulation containing an cyclic-GMP-specific phosphodiesterase type 5 (PDE5), dextromethorphan and optionally an agent which inhibits the oxidative activity of cytochrome-P450, such as a naphthyridine, xanthine, phenoxy amino alkane, carbamoyl imidazole, guanidine imidazole, e.g. cimetidine (N-cyano-N'-methyl-N"-[2 [[(5-methyl-1H-imidazol-4 yl)methyl]thio]ethyl] guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime. Administration of the pharmaceutical formulation is carried out within the context of a predetermined dosing regimen such that the agent is effective in the treatment of premature ejaculation. Drug delivery may be accomplished through any route effective to provide relief from premature ejaculation, including oral, parenteral, buccal, rectal, topical, transdermal, transurethral, and intracavernosal injection.

Additional objects, advantages and novel features of the invention will be set forth in part in the description which follows, and in part will become apparent to those skilled in the art upon examination of the following, or may be learned by practice of the invention.

DETAILED DESCRIPTIONS OF THE INVENTION

Figure 1:
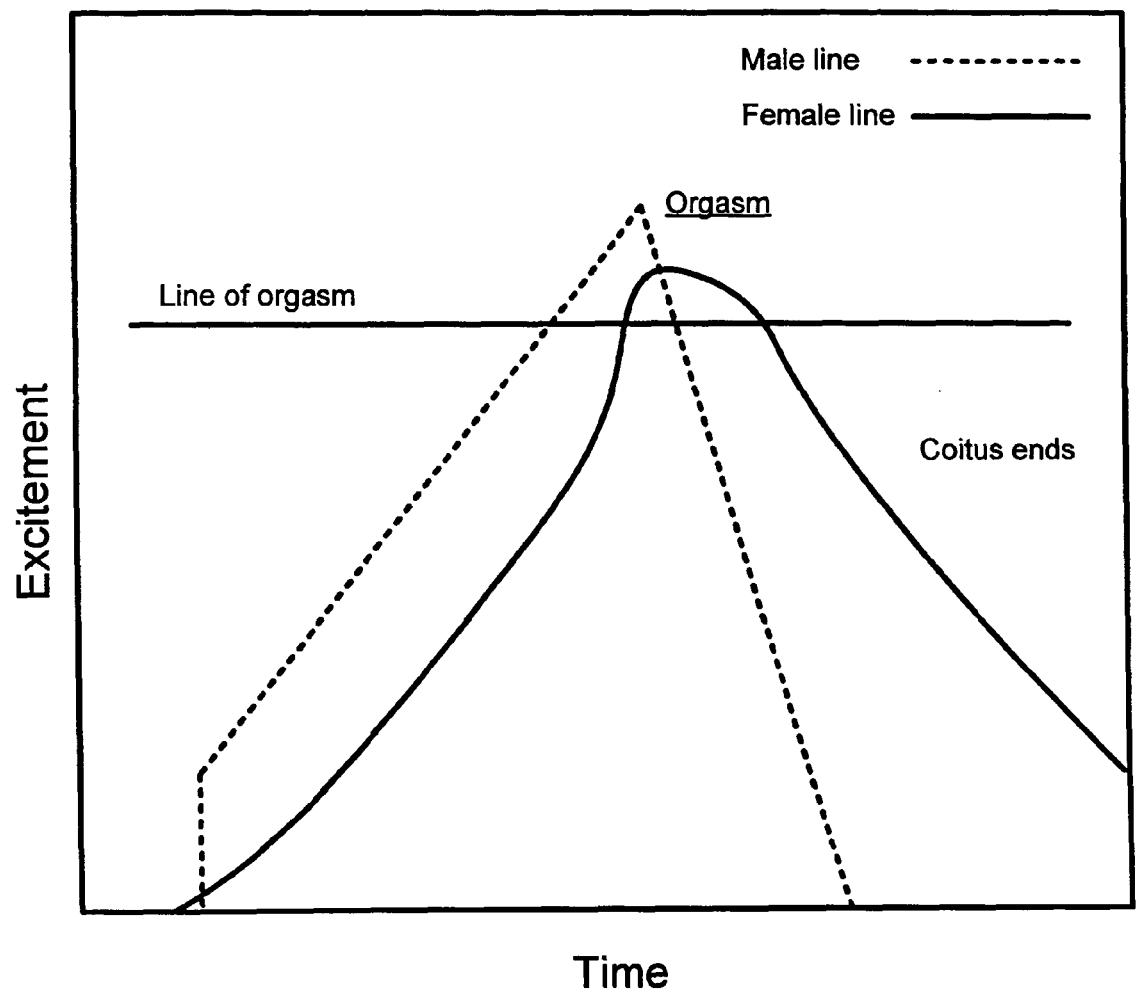
FIG. 1 illustrates the orgasm levels in a man and woman during the normal Sexual intercourse. (The orgasm level is an arbitrary quantity describing the physical and emotional excitements during sexual intercourse.)
Figure 2:
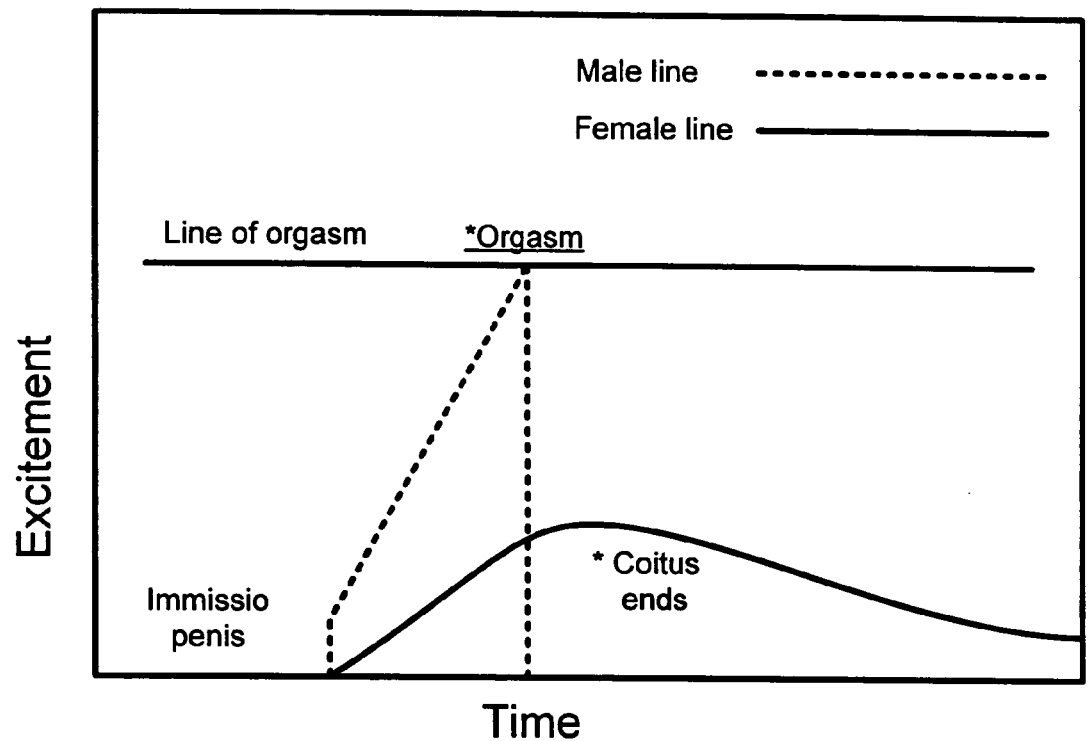
FIG. 2 illustrates the orgasm levels in male and female in the case of pre-mature ejaculation. (The orgasm level is an arbitrary quantity describing the physical and emotional excitements during sexual intercourse.)

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting. It must be noted that, as used in this specification and the appended claims, the singular forms "a," "an" and "the" include plural referents unless the context clearly dictates otherwise. Thus, for example, reference to "a pharmacologically active agent" includes a combination of two or more pharmacologically active agents, and the like. In describing and claiming the present invention, the following terminology will be used in accordance with the definitions set out below. The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect. The term "topical administration" is used in its conventional sense to mean delivery of a topical drug or pharmacologically active agent to the skin or mucosa. "Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner. By an "effective" amount of a drug or pharmacologically active agent is meant a nontoxic but sufficient amount of the drug or agent to provide the desired effect.

The term "premature ejaculation" as used herein intends a sexual dysfunction wherein a male is unable to control the ejaculatory process to a degree sufficient to satisfy a partner. Generally, "premature ejaculation" refers to persistent or recurring ejaculation with minimal stimulation before or during sexual intercourse. The term includes both "congenital" or "lifelong" premature ejaculation and "primary" or "acquired" premature ejaculation as set forth, for example, in U.S. Pat. No. 5,151,448, and in Male Infertility and Sexual Dysfunction at p. 356 (New York: Springer-Verlag, 1997). See also Diagnostic and Statistical Manual of Mental Disorders (Washington, D.C.: American Psychiatric Association, 1994).

The term "NSAID" refers to non-steroidal substances which inhibit the production of prostaglandins by binding with cyclo-oxygenase enzymes. The compound acetaminophen is included under this category even though acetaminophen does not have anti-inflammatory properties but bind with cyclo-oxygenase enzymes in the periphery and at the hypothalamic thermoregulatory center.

The term "sildenafil" as used herein includes the free base form of this compound as well as pharmacologically acceptable acid addition salts thereof formed with organo-carboxylic acids, organo-sulphonic acids or inorganic acids. For purposes of the present invention, the organo-carboxylic acid salt, sildenafil citrate, having a solubility in water of 3.5 mg/ml is particularly preferred. Reference to "sildenafil" includes sildenafil citrate.

The present inventor was searching for an effective treatment of premature ejaculation. Based on the previous arts described above the inventor reasoned that in order to control the ejaculation process for males who do not have any erection problem and to have satisfactory sexual intercourse, two steps have to be preferred (hereinafter referred to as CLASS I); (1) the blood flow to the penis has to be modulated so that the male will have longer time to achieve full erection and the sexual partners will have sufficient time for foreplay to reach sexual arousal; (2) the ejaculation process has to be delayed so that the sexual partners would have sufficient time for intercourse to reach maximum sexual satisfaction.

In the case of males who have erection problem and can not control ejaculation once erection is achieved the following two steps have to be preferred; (1) the erection has to be achieved through certain pharmaceutical agents such as sildenafil such that the male will have full erection upon the stimulation by the sexual partner; (2) the ejaculation process has to be delayed so that the sexual partners would have sufficient time for intercourse to reach maximum sexual satisfaction (hereinafter referred to as CLASS II).

It is understood from the information presented in the background that anti-inflammation agents which regulate prostaglandin synthetic pathways in humans would have an effect on the blood flow and the subsequent erection of the male penis and administration of these anti-inflammatory agents would have a modulation effect on the erection and the hardness of the male penis. Further, these anti-inflammatory agents will have anti-stimulatory effects on smooth muscle such as that of the male penis. It is understood that the administration of DM has the anti-excitotoxic effect in humans and the administration of DM to human male would have an effect on the ejaculation process. Further it is understood that administration of a debrisoquin hydroxylase inhibitor or a cytochrome-P450 inhibitor concurrently with DM substantially increases the observable therapeutic effects of DM in human clinical trials, then the effectiveness of DM as an agent for treating premature ejaculation can also be increased by the co-administration of a cytochrome oxidase inhibitor. Based on these observations the inventors reasoned that administration of a combination of these agents would have a therapeutical effect on premature ejaculation for CLASS I males. To their surprise, they now discovered that ingestion of these agents indeed has profound effects on the premature ejaculation and that they prolong the sexual intercourse to reach maximal orgasm. Further they observed that these agents can be used to have multiple orgasm during sexual intercourse.

In addition, the inventors have discovered that ingestion of sildenafil and DM has profound effects on the premature ejaculation in CLASS II males and that they prolong the sexual intercourse to reach maximal orgasm. Further they observed that these agents can be used to have multiple orgasm during sexual intercourse. Further the inventor has discovered that ingestion of acetaminophen or other NSAIDS along with sildenafil and DM does not affect the therapeutical effect of sildenafil and DM combination in treating premature ejaculation in CLASS II patients.

Active Agents for Treating Premature Ejaculation in Class I Males

In order to carry out the method of the invention to treat premature ejaculation in CLASS I males, selected pharmacologically active agent is administered to an individual. The active agents may be administered orally, parenterally, buccally, rectally, or locally by intracavernosal injection or by delivery to the urethra. Suitable pharmacologically active agents include: anti-inflammatory agents salicylates, acetaminophen, Diclofenac sodium, Etodolac, fenoprofen calcium, flurbiprofen, ibuprofen, ketoprofen, meclofenamate sodium monohydrate, nabumetone, naproxen, naproxen sodium, oxaprozin, phenylbutazone, piroxicam, sulindac, tolmetin sodium, hydroxychloroquine sulfate, penicillamine, sulfasalazine, aurothioglucose, gold sodium thiomalate, auranofin, and the like; anti-excitotoxic agents dextromethorphan and the like; cytochrome-P450 inhibitors quinine, quinidine, naphthyridine, xanthine, phenoxy amino alkane, carbamoyl imidazole, guanidine imidazole, e.g. cimetidine (N-cyano-N'-methyl-N''-[2[[(5-methyl-1H-imidazol-4yl) methyl]thio]ethyl]guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime and the like.

PGE2, PGF2α, PGF2β, PGA2, and PGB2, and their esters and pharmacologically acceptable salts, are extemely potent in causing various biological responses. Several anti-inflammatory agents interfere in the biosynthetic pathways of prostaglandin and thereby modulate the biological effects of prostaglandin in humans.

Dextromethorphan acts at a class of neuronal receptors known as sigma receptors. They are inhibitory receptors, which means that their activation by DM or other sigma agonists causes the suppression of certain types of nerve signals. Dextromethorphan also acts at another class of receptors known as N-methyl-D-aspartate (NMDA) receptors, which are one type of excitatory amino acid (EAA) receptor. Unlike its agonist activity at sigma receptors, DM acts as an antagonist at NMDA receptors, which means that DM suppresses the transmission of nerve impulses mediated via NMDA receptors. Since NMDA receptors are excitatory receptors, the activity of DM as an NMDA antagonist also leads to the suppression of certain types of nerve signals. The anti-excitotoxic activity of dextromethorphan and dextrorphan, and the blockade of NMDA receptors by these drugs, are discussed in items such as Choi 1987, Wong et al 1988, Steinberg et al 1988, and U.S. Pat. No. 4,806,543 (Choi 1989). Dextromethorphan has also been reported to suppress activity at neuronal calcium channels (Carpenter et al 1988). Dextromethorphan and the receptors it interacts with are further discussed in Tortella et al 1989, Leander 1989, Koyuncuoglu & Saydam 1990, Ferkany et al 1988, George et al 1988, Prince & Feeser 1988, Feeser et al 1988, Craviso and Musacchio 1983, and Musacchio et al 1988.

DM disappears fairly rapidly from the bloodstream (see, e.g., Vetticaden et al 1989 and Ramachander et al 1977). DM is converted in the liver to two metabolites called dextrorphan and 3-methoxymorphinan, by an enzymatic process called O-demethylation. This enzyme is usually referred to as debrisoquin hydroxylase, since it was discovered a number of years ago to carry out a hydroxylation reaction on debrisoquin. It is also referred to in various articles as P450 DB or P450-2D6. A number of compounds inhibit the activity of the debrisoquin hydroxylase (sparteine monooxygenase) isozyme; see Inaba et al 1985. The most powerful of these inhibitors is quinidine, a dextrorotatory stereoisomer of quinine; it is normally used to treat cardiac arrhythmias. Inaba et al 1986 and Nielsen et al 1990 discuss the ability of quinidine to inhibit the oxidation of sparteine in in vivo animal tests, and Brinn et al 1986, Brosen et al 1987, and Broly et al 1989 discuss the ability of quinidine to inhibit DM metabolism in liver cell preparations. In addition to the inhibition of debrisoquin hydroxylase, which is exceptionally potent and easily demonstrated, other cytochrome P450 isozymes are also likely to be suppressed by quinidine, with varying levels of binding affinity. Accordingly, even though quinidine exerts its most marked effect on debrisoquin hydroxylase, it is likely to suppress a number of other cytochrome P450 enzymes as well, thereby subjecting a patient to a more general loss of normal and desirable liver activity. The primary oxidized metabolic product of dextromethorphan is dextrorphan, which is widely believed among neurologists to be active in exactly the same manner as dextromethorphan; both drugs reportedly are sigma agonists, NMDA antagonists, and calcium channel antagonists. It has been shown that the administration of a compound which inhibits debrisoquin hydroxylase, in conjunction with DM, causes a major increase in the concentration and stability of DM in the blood of patients, compared to patients who receive only DM; and the administration of a debrisoquin hydroxylase inhibitor in conjunction with DM has a clear and substantial impact on the detectable effects of DM in humans. Eventhough debrisoquin hydroxylase inhibitors are preferred in the potentiating activity of Dextromethorphan, other agents which inhibit the oxidative activity of cytochrome-P450, such as a naphthyridine, xanthine, phenoxy amino alkane, carbamoyl imidazole, guanidine imidazole, e.g. cimetidine (N-cyano-N'-methyl-N''-[2[[(5-methyl-1H-imidazol-4 yl)methyl]thio]ethyl] guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime may be useful in potentiating the activity of dextromethorphan.

In order to practice the invention, any one of the NSAID substances can be used. However, the invention is illustrated by using acetaminophen which is most commonly used under the brand name Tylenol. Similar in mechanism to aspirin, acetaminophen is a weak inhibitor of cyclo-oxygenase in the periphery and at the hypothalamic thermoregulatory center. It has antipyretic and analgesic effects, but no anti-inflammatory effect. Acetaminophen is relatively safe at normal dosages. Acetaminophen is able to cross the blood-brain barrier, unlike the NSAIDs and may be able to inhibit prostaglandin synthesis whether they are formed centrally or peripherally. It Inhibits synthesis of prostaglandins by competing with arachidonic acid for the active site on the COX enzyme and COX isoenzyme that is most sensitive to the antipyretic activity of acetaminophen is more susceptible than either COX-1 or COX-2 which suggests the presence of either cell-specific factors that produce and altered COX-2 or possibly the presence of a COX-3 isoenzyme.

Oral combination dosage units preferably contain dextromethorphan in the range of about 30 to not more than 200 milligrams (mg), preferably in the range of about 60 and about 120 mg and of acetaminophen in the range of about 300 to about 1500 mg, preferably in the range of about 600 to about 1200 mg, so long as the combined dose received by the patient is accompanied by minimal or substantially no undesirable side effects. A particularly preferred oral combination dosage unit contains about 120 mg dextromethorphan and not more than 1200 mg acetaminophen, more preferably about 90 mg dextromethorphan and not more than about 1000 mg acetaminophen.

Alternatively, the dextromethorphan and acetaminophen may be formulated separately in the foregoing compositions as the sole active ingredient for practicing sequential administration of each respective drug.

For sequential administration therapy, acetaminophen and dextromethorphan each is administered in a separate dosage. For sequential administration of acetaminophen, the dosage unit preferably contains acetaminophen in a range of about 200 to about 1500 mg, more preferably in the range of about 500 to about 1200 mg, and for administration of dextromethorphan the dosage unit preferably contains dextromethorphan in a range of about 30 to not more than 120 mg, more preferably in the range of about 60 to about 90 mg so long as the total combined dose received by the patient is accompanied by minimal or substantially no undesirable side effects.

A particularly preferred sequential administration dosage unit of acetaminophen contains acetaminophen in the range of about 600 to about 1000 mg and of dextromethorphan contains dextromethorphan in the range of about 45 to about 90 mg. Preferably, each drug is administered orally. Alternatively, each drug can be administered by different oral routes; i.e., one can be ingested and the other administered sublingually or by buccal patch.

For effective sequential administration of acetaminophen and dextromethorphan, the release of each drug is preferably staggered to maximize the beneficial delayed ejaculation by acetaminophen.

In order to potentiate the effect of dextromethorphan, optionally an effective amount of a cytochrome P450 enzyme inhibitor such as quinidine can be administered to the patient either in a combination dosage unit or in a sequential administration dosage unit. When a cytochrome P450 inhibitor is administered in order to augment the effect of dextromethorphan, the dosage of dextromethorphan can be suitably adjusted to have maximum efficacy with minimum side effects. Oral combination dosage units preferably can contain quinidine in the range of about 50 to not more than 200 milligrams (mg), preferably in the range of about 90 and about 120 mg. Oral combination dosage units preferably can contain quinidine in the range of about 50 to not more than 200 milligrams (mg), preferably in the range of about 90 and about 120 mg.

Active Agents for Treating Premature Ejaculation in Class II Males

In order to carry out the method of the invention to treat premature ejaculation in CLASS II males who have erection as well as ejaculation problems, selected pharmacologically active agent is administered to an individual. The active agents may be administered orally, parenterally, buccally, rectally, or locally by intracarvernosal injection or by delivery to the urethra. Suitable pharmacologically active agents include, cyclic-GMP-specific phosphodiesterase type 5 (PDE5) inhibitors such as sildenafil, anti-excitotoxic agents such as dextromethorphan and optionally the cytochrome-P450 inhibitors such as quinine, quinidine, naphthyridine, xanthine, phenoxy amino 11 alkane, carbamoyl imidazole, guanidine imidazole, e.g. cimetidine (N-cyano-N'-methyl-N"-[2 [[(5-methyl-1H-imidazol-4yl)methyl]thio]ethyl] guanidine), quinoline, e.g. chloroquine (7-chloro-4-(4-diethylamino-1-methylbutylamino)quinoline) and primaquine (8-(4-amino-1-methylbutylamino)-6-methoxyquinoline), a trifluoromethyl oxime ether, e.g., fluvoxamine, also known as 5-methoxy-1-[4-(trifluoromethyl)-phenyl]-1 pentanone 0-(2-aminoethyl) oxime.

Figure 3A:
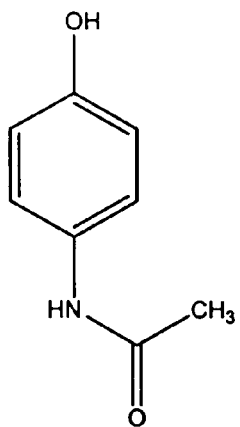
FIGS. 3A-3D illustrate the chemical structures of certain compounds which may be used in practicing the present invention.
Figure 3B:
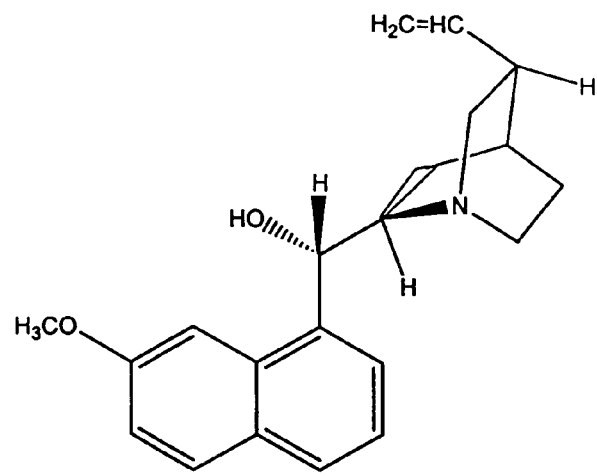
Figure 3C:
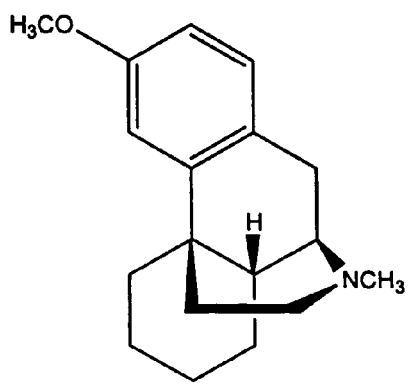
Figure 3D:
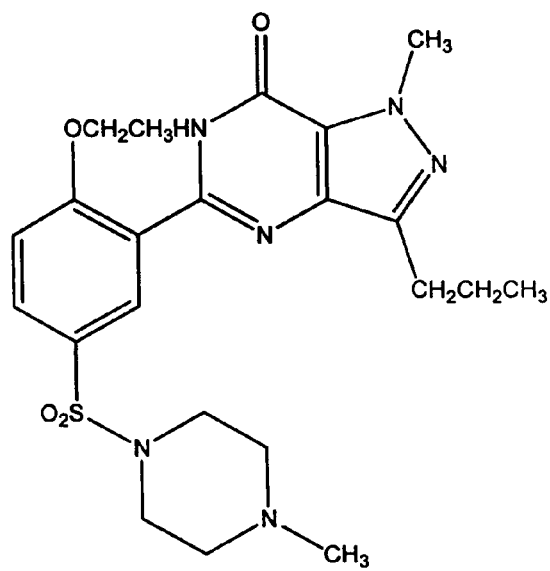

Sildenafil is designated chemically as 1-[[3-(6,7-dihydro-1-methyl-7-oxo-3-propyl-1H-pyrazolo[4,3-d]pyrimidin-5-yl)-4-ethoxyphenyl]sulfonyl]-4-methyl piperazine and has the following structural formula: FIG. 3.

Sildenafil citrate is presently the active ingredient of a commercial medication for impotence sold under the designation Viagra™ (Pfizer Labs, N.Y.) formulated in tablets equivalent to 25 mg, 50 mg and 100 mg sildenafil for oral administration. According to the manufacturer, in addition to the active ingredient, sildenafil citrate, each tablet contains the following inactive ingredients: microcrystalline cellulose, anhydrous dibasic calcium phosphate, croscarmellose sodium, magnesium stearate, hydroxypropyl methylcellulose, titanium dioxide, lactose, triacetin, and FD&C Blue #2 aluminum lake.

It is known from in vitro studies that sildenafil is approximately 4,000 fold more selective for inhibiting phosphodiesterase type 5 (PDE5) than on other known phosphodiesterases, such as PDE3, which is involved in control of cardiac contractility. Sildenafil is reportedly only about 10-fold as potent for PDE5 compared to PDE6, an enzyme found in the retina and it is this lower selectivity which is thought to be the basis for abnormalities related to color vision observed with higher doses or plasma levels.

Sildenafil, administered as the commercially available Viagra™ formulation, is reported to be rapidly absorbed after oral administration, with absolute bioavailability of about 40%. Its pharmacokinetics are dose-proportional over the recommended dose range. Based on the Viagra™ manufacturer's product literature, maximum observed plasma concentrations are reached within 30 to 120 minutes (median 60 minutes) of oral dosing in the fasted state. When the Viagra™ formulation is taken with a high fat meal, the rate of absorption is reduced, with a mean delay in Tmax of 60 minutes and mean reduction in Cmax of 29%. The mean steady state volume of distribution (Vss) for sildenafil is reportedly 105 L, indicating distribution into the tissues. Based upon reported measurements of sildenafil in the semen of healthy volunteers 90 minutes after dosing, less than 0.001% of the administered dose appeared in the semen of the patients.

Surprisingly, a therapeutically effective dosage combination of dextromethorphan and sildenafil employed with the compositions of this invention maximizes the beneficial erectogenic efficacy of sildenafil by delaying the premature ejaculation.

Oral combination dosage units preferably contain dextromethorphan in the range of about 30 to not more than 120 milligrams (mg), preferably in the range of about 50 and about 100 mg and of sildenafil in the range of about 10 to about 75 mg, preferably in the range of about 15 to about 50 mg, so long as the combined dose received by the patient is accompanied by minimal or substantially no undesirable side effects. A particularly preferred oral combination dosage unit contains about 100 mg dextromethorphan and not more than 100 mg sildenafil, more preferably about 75 mg dextromethorphan and not more than about 50 mg sildenafil.

Alternatively, the dextromethorphan and sildenafil may be formulated separately in the foregoing compositions as the sole active ingredient for practicing sequential administration of each respective drug.

For sequential administration therapy, sildenafil and dextromethorphan each is administered in a separate dosage. For sequential administration of sildenafil, the dosage unit preferably contains sildenafil in a range of about 10 to about 120 mg, more preferably in the range of about 25 to about 100 mg, and for administration of dextromethorphan the dosage unit preferably contains dextromethorphan in a range of about 30 to not more than 120 mg, more preferably in the range of about 60 to about 90 mg so long as the total combined dose received by the patient is accompanied by minimal or substantially no undesirable side effects.

A particularly preferred sequential administration dosage unit of sildenafil contains sildenafil in the range of about 50 to about 100 mg and of dextromethorphan contains dextromethorphan in the range of about 45 to about 90 mg. Preferably, each drug is administered orally. Alternatively, each drug can be administered by different oral routes; i.e., one can be ingested and the other administered sublingually or by buccal patch.

If desired, to facilitate absorption and thus bioavailability, absorption enhancing agents, such as cyclodextrins, particularly β-cyclodextrin, or a derivative thereof, such as hydroxypropyl-β-cyclodextrin (HPBCD) and the like may be included. Cyclodextrins are a group of cyclic, nonreducing oligosaccharides built up from six, seven or eight glucopyranose rings, respectively known as alpha, beta and gamma cyclodextrins. The cyclodextrins are a class of cavity-containing cyclic compounds possessing the property of forming a molecular inclusion complexes, which anchor or entrap another chemical compounds without the formation of covalent bonds. HPBCD is a cyclic polymer having a doughnut-shaped molecular structure including an inner cavity.

Hydroxypropyl-β-cyclodextrins are commercially available compounds that are derived from β-cyclodextrins by condensation with a propylene oxide to provide the corresponding hydroxypropyl derivatives having a degree of substitution (D.S.) of up to about 15 or higher. For the purposes of the present invention a D.S. value of about 5 to 7 is preferred.

The preparation of such suitable hydroxypropyl-β-cyclodextrins is described, inter alia, in the International Journal of Pharmaceutics, 29, 73-82 (1986) and in the Journal of Pharmaceutical Sciences, 75 (6), 571-572 (1986). Also known and suitable for the present invention are the hydroxypropyl-β-cyclodextrins that are polyethers of cyclodextrins and are obtained by the condensation of an excess of hydroxypropylene oxide with β-cyclodextrin as described in U.S. Pat. No. 3,459,731. to Gramera et al. Hydroxypropyl-β-cyclodextrin (HPBCD) is particularly preferred cyclodextrin constituent, but is not limited thereto. The weight percent of the HPBCD in the composition is preferably in the range of about 1 to about 10 weight percent of the total composition.

Particularly in the case of sildenafil, it has been found that HPBCD enhances bioavailability. Thus, the desired therapeutic effect can be achieved with a relatively lower dose of sildenafil, thereby minimizing the likelihood of adverse affects.

For effective sequential administration of sildenafil and dextromethorphan, the release of each drug is preferably staggered to maximize the beneficial prolongation of erection by dextromethorphan and maintenance of erection by sildenafil upon sexual stimulation.

To augment the beneficial effect of dextromethorphan and sildenafil therapy, lesser amounts of erectogenic agents can be included. The term "erectogenic agents" as used herein refers to adrenal steroids, such as testosterone, dehydroepiandrosterone (DHEA) and the like. Preferably, the erectogenic agents are added in an amount in the range of about 5 to about 10 percent by weight, more preferably in the range of about 6 to about 8 percent by weight of the weight of sildenafil administered.

In order to potentiate the effect of dextromethorphan, optionally an effective amount of a cytochrome P450 enzyme inhibitor such as quinidine can be administered to the patient either in a combination dosage unit or in a sequential administration dosage unit. When a cytochrome P450 inhibitor is administered in order to augment the effect of dextromethorphan, the dosage of dextromethorphan can be suitably adjusted to have maximum efficacy with minimum side effects. Oral combination dosage units preferably can contain quinidine in the range of about 50 to not more than 200 milligrams (mg), preferably in the range of about 90 and about 120 mg. Oral combination dosage units preferably can contain quinidine in the range of about 50 to not more than 200 milligrams (mg), preferably in the range of about 90 and about 120 mg.

In addition, suitable amount of a COX inhibitor can be added to the composition of the invention containing sildenafil and dextromethorphan without affecting the therapeutic effect of the composition.

The active agents may be administered in the form of pharmaceutically acceptable salts, esters, amides or prodrugs or combinations thereof. However, conversion of inactive ester, amide or prodrug forms to an active form must occur prior to or upon reaching the target tissue or cell. Salts, esters, amides and prodrugs of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base (typically wherein the neutral form of the drug has a neutral—$NH_2$ group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, ptoluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on a drug are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature. In addition, chiral active agents may be in enantiomerically pure form, or they may be administered as an enantiomeric mixture.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drugs in combination with a pharmaceutically acceptable carrier and, in addition, may include other pharmaceutical agents, adjuvants, diluents, buffers, etc. The compounds may thus be administered orally, parenterally, transdermally, rectally, nasally, buccally, topically or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. Actual methods of preparing such dosage forms are known, or will be apparent, to those skilled in this art; for example, see Remington's Pharmaceutical Sciences, referenced above. For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained. See, e.g., U.S. Pat. No. 3,710,795.

The active agent can be administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred. Depending on the drug administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co. Irvine, Calif.), SEPA® (available from Macrochem Co., Lexington, Mass.), alcohols (e.g., ethanol), detergents (such as Tergitol®, Nonoxynol-9® and TWEEN-80®) and the like.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Plasma Concentrations of DM

Five patients with a symptom of having premature ejaculation were orally administered 120 mg of DM, with no co-administration of quinidine. Between 10 and 12 hours later, blood was sampled, blood plasma was isolated by centrifugation, and the plasma was analyzed to determine the DM concentration using the HPLC method. During a different week, the same patients were orally administered 60 mg of DM (half the control dosage) and 150 mg of quinidine. Between 10 and 12 hours later, blood was sampled and the plasma was analyzed for DM using thebaine/HPLC. The results, in Table 1, indicate that quinidine causes a major increase in the concentration of DM in the blood plasma.

TABLE 1

Effect of Quanidine on Plasma Concentration of DM

| Volunteer Number | DM DOSAGE (mg) | QUINIDINE DOSAGE (mg) | PLASMA CONCENTRATION (ng/mL) |
| --- | --- | --- | --- |
| 1 | 120 | 0 | <1 |
|   | 60  | 150 | 10.2 |
| 2 | 120 | 0 | 5.7 |
|   | 60  | 150 | 34.2 |
| 3 | 120 | 0 | 13.5 |
|   | 60  | 150 | 42.4 |
| 4 | 120 | 0 | 15.4 |
|   | 60  | 150 | 30.2 |
| 5 | 120 | 0 | <1 |
|   | 60  | 150 | 26.8 |

EXAMPLE 2

Capsule Formulations

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

|  | In each | In 100 |
| --- | --- | --- |
| Capsule Formulation 1 |  |  |
| Acetaminophen | 200 mg | 20.0 g |
| Dextromethorphan Hydrobromide MonoHydrate | 20 mg | 2.0 g |
| Quinidine Sulphate Dihydrate | 40 mg | 4.0 g |
| Starch (potato) | 120 mg | 12.0 g |
| Mannitol USP | 50 mg | 5.0 g |

-continued

|  | In each | In 100 |
|---|---|---|
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |

Capsule Formulation 2

|  | In each | In 100 |
|---|---|---|
| Acetaminophen | 100 mg | 10.0 g |
| Dextromethorphan Hydrobromide MonoHydrate | 30 mg | 3.0 g |
| Quinidine Sulphate Dihydrate | 40 mg | 4.0 g |
| Starch (potato) | 50 mg | 5.0 g |
| Mannitol USP | 210 mg | 21.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |

Capsule Formulation 3

|  | In each | In 100 |
|---|---|---|
| Acetaminophen | 200 mg | 20.0 g |
| Dextromethorphan Hydrobromide MonoHydrate | 40 mg | 4.0 g |
| Quinidine Sulphate Dihydrate | 40 mg | 4.0 g |
| Starch (potato) | 100 mg | 10.0 g |
| Mannitol USP | 50 mg | 5.0 g |
| Microcrystalline Cellulose<sup>a</sup> | 58 mg | 5.8 g |
| Magnesium Stearate | 10 mg | 1.0 g |
| Talc | 2 mg | 0.2 g |
| Total Solid | 500 mg | 50.0 g |

Capsule Formulation 4

|  | In each | In 100 |
|---|---|---|
| Acetaminophen | 200 mg | 20.0 g |
| Dextromethorphan Hydrobromide MonoHydrate | 20 mg | 2.0 g |
| Quinidine Sulphate Dihydrate | 40 mg | 4.0 g |
| Starch(potato) | 120 mg | 12.0 g |
| Lactose | 50 mg | 5.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |

Capsule Formulation 5

|  | In each | In 100 |
|---|---|---|
| Acetaminophen | 200 mg | 20.0 g |
| Dextromethorphan Hydrobromide MonoHydrate | 20 mg | 2.0 g |
| Quinidine Sulphate Dihydrate | 40 mg | 4.0 g |
| Lactose | 100 mg | 10.0 g |
| Mannitol USP Granular | 58 mg | 5.8 g |
| Microcrystalline Cellulose<sup>a</sup> | 50 mg | 5.0 g |
| Stearic acid | 10 mg | 1.0 g |
| Silica gel | 20 mg | 2.0 g |
| Total Solid | 500 mg | 50.0 g |

Capsule Formulation 6

|  | In each | In 100 |
|---|---|---|
| Acetaminophen | 100 mg | 10.0 g |
| Dextromethorphan Hydrobromide MonoHydrate | 60 mg | 6.0 g |
| Quinidine Sulphate Dihydrate | 40 mg | 4.0 g |
| Starch(potato) | 80 mg | 8.0 g |
| Mannitol USP | 100 mg | 10.0 g |
| Microcrystalline Cellulose<sup>a</sup> | 80 mg | 8.0 g |
| Magnesium stearate | 20 mg | 2.0 g |
| Silica gel | 20 mg | 2.0 g |
| Total Solid | 500 mg | 50.0 g |

Capsule Formulation 7

|  | In each | In 100 |
|---|---|---|
| Acetaminophen | 200 mg | 20.0 g |
| Dextromethorphan Hydrobromide MonoHydrate | 60 mg | 6.0 g |
| Quinidine Sulphate Dihydrate | 40 mg | 4.0 g |
| Starch(potato) | 100 mg | 10.0 g |
| Mannitol USP | 100 mg | 10.0 g |
| Total Solid | 420 mg | 42.0 g |

Capsule Formulation 8

|  | In each | In 100 |
|---|---|---|
| Acetaminophen | 100 mg | 10.0 g |
| Dextromethorphan Hydrobromide MonoHydrate | 40 mg | 4.0 g |
| Quinidine Sulphate Dihydrate | 20 mg | 2.0 g |
| Starch(potato) | 100 mg | 10.0 g |
| Mannitol USP | 100 mg | 10.0 g |
| Microcrystalline Cellulose<sup>a</sup> | 60 mg | 6.0 g |
| Stearic acid | 50 mg | 5.0 g |
| Colloidal Silica | 20 mg | 2.0 g |
| Talc | 10 mg | 1.0 g |
| Total Solid | 500 mg | 50.0 g |

Capsule Formulation 9

|  | In each | In 100 |
|---|---|---|
| Acetaminophen | 200 mg | 20.0 g |
| Dextromethorphan Hydrobromide MonoHydrate | 40 mg | 4.0 g |
| Quinidine Sulphate Dihydrate | 60 mg | 6.0 g |
| Lactose | 50 mg | 5.0 g |
| Mannitol USP | 40 mg | 4.0 g |
| Microcrystalline Cellulose<sup>a</sup> | 50 mg | 5.0 g |
| Stearic acid | 40 mg | 4.0 g |
| Silica gel | 20 mg | 2.0 g |
| Total Solid | 500 mg | 50.0 g |

Capsule Formulation 10

|  | In each | In 100 |
|---|---|---|
| Acetaminophen | 100 mg | 10.0 g |
| Dextromethorphan Hydrobromide MonoHydrate | 40 mg | 4.0 g |
| Quinidine Sulphate Dihydrate | 60 mg | 6.0 g |
| Lactose | 40 mg | 4.0 g |
| Mannitol USP | 160 mg | 16.0 g |
| Microcrystalline Cellulose<sup>a</sup> | 50 mg | 5.0 g |
| Magnesium Stearate | 30 mg | 3.0 g |
| Talc | 20 mg | 2.0 g |
| Total Solid | 500 mg | 50.0 g |

Capsule Formulation 11

|  | In each | In 100 |
|---|---|---|
| Acetaminophen | 200 mg | 20.0 g |
| Dextromethorphan Hydrobromide MonoHydrate | 40 mg | 4.0 g |
| Lactose | 100 mg | 10.0 g |
| Mannitol USP | 60 mg | 6.0 g |
| Microcrystalline Cellulose<sup>a</sup> | 50 mg | 5.0 g |
| Magnesium Stearate | 30 mg | 3.0 g |
| Talc | 20 mg | 2.0 g |
| Total Solid | 500 mg | 50.0 g |

Capsule Formulation 12

|  | In each | In 100 |
|---|---|---|
| Acetaminophen | 200 mg | 10.0 g |
| Dextromethorphan Hydrobromide MonoHydrate | 60 mg | 6.0 g |
| Lactose | 80 mg | 8.0 g |
| Mannitol USP | 160 mg | 16.0 g |
| Microcrystalline Cellulose<sup>a</sup> | 50 mg | 5.0 g |
| Magnesium Stearate | 30 mg | 3.0 g |
| Talc | 20 mg | 2.0 g |
| Total Solid | 500 mg | 50.0 g |

Capsule Formulation 13

|  | In each | In 100 |
|---|---|---|
| Celecoxib | 20 mg | 2.0 g |
| Dextromethorphan Hydrobromide MonoHydrate | 30 mg | 3.0 g |
| Starch (potato) | 250 mg | 25.0 g |
| Mannitol USP | 130 mg | 13.0 g |

-continued

|  | In each | In 100 |
|---|---|---|
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 14 | | |
| Celecoxib | 30 mg | 3.0 g |
| Dextromethorphan Hydrobromide MonoHydrate | 40 mg | 4.0 g |
| Starch (potato) | 230 mg | 23.0 g |
| Mannitol USP | 130 mg | 13.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 15 | | |
| Celecoxib | 30 mg | 3.0 g |
| Dextromethorphan Hydrobromide MonoHydrate | 40 mg | 4.0 g |
| Quinidine Sulphate Dihydrate | 40 mg | 4.0 g |
| Starch (potato) | 190 mg | 19.0 g |
| Mannitol USP | 130 mg | 13.0 g |
| Microcrystalline Cellulose<sup>a</sup> | 58 mg | 5.8 g |
| Magnesium Stearate | 10 mg | 1.0 g |
| Talc | 2 mg | 0.2 g |
| Total Solid | 500 mg | 50.0 g |
| Capsule Formulation 16 | | |
| Rofecoxib | 10 mg | 1.0 g |
| Dextromethorphan Hydrobromide MonoHydrate | 30 mg | 3.0 g |
| Quinidine Sulphate Dihydrate | 20 mg | 2.0 g |
| Starch(potato) | 240 mg | 24.0 g |
| Lactose | 130 mg | 13.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 17 | | |
| Rofecoxib | 20 mg | 2.0 g |
| Dextromethorphan Hydrobromide MonoHydrate | 30 mg | 3.0 g |
| Starch(potato) | 250 mg | 25.0 g |
| Lactose | 130 mg | 13.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 18 | | |
| Rofecoxib | 30 mg | 3.0 g |
| Dextromethorphan Hydrobromide MonoHydrate | 40 mg | 4.0 g |
| Starch(potato) | 230 mg | 23.0 g |
| Lactose | 130 mg | 13.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |

EXAMPLE 3

Capsule Formulations Containing Sildenafil

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

|  | In each | In 100 |
|---|---|---|
| Capsule Formulation 1 | | |
| Sildenafil Citrate | 25 mg | 2.5 g |
| Dextromethorphan Hydrobromide MonoHydrate | 45 mg | 4.5 g |
| Starch (potato) | 220 mg | 22.0 g |
| Mannitol USP | 140 mg | 14.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 2 | | |
| Sildenafil Citrate | 25 mg | 2.5 g |
| Dextromethorphan Hydrobromide MonoHydrate | 45 mg | 4.5 g |
| Quinidine Sulphate Dihydrate | 40 mg | 4.0 g |
| Starch (potato) | 200 mg | 20.0 g |
| Mannitol USP | 120 mg | 12.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 3 | | |
| Acetaminophen | 250 mg | 25.0 g |
| Sildenafil Citrate | 25 mg | 2.5 g |
| Dextromethorphan Hydrobromide MonoHydrate | 45 mg | 4.5 g |
| Starch (potato) | 100 mg | 10.0 g |
| Mannitol USP | 10 mg | 1.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 4 | | |
| Acetaminophen | 325 mg | 32.5 g |
| Sildenafil Citrate | 25 mg | 2.5 g |
| Dextromethorphan Hydrobromide MonoHydrate | 45 mg | 4.5 g |
| Starch (potato) | 25 mg | 2.5 g |
| Mannitol USP | 10 mg | 1.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |
| Capsule Formulation 5 | | |
| Acetaminophen | 325 mg | 32.5 g |
| Sildenafil Citrate | 12.5 mg | 1.25 g |
| Dextromethorphan Hydrobromide MonoHydrate | 45 mg | 4.5 g |
| Starch (potato) | 37.5 mg | 3.75 g |
| Mannitol USP | 10 mg | 1.0 g |
| Microcrystalline Cellulose<sup>a</sup> | 58 mg | 5.8 g |
| Stearic acid | 10 mg | 1.0 g |
| Silica gel | 2 mg | 0.2 g |
| Total Solid | 500 mg | 50.0 g |

EXAMPLE 4

A white male, born on May 3, 1957 was in the process of establishing a cosmetic business. He was in the midst of setting up and manufacturing several products, making strategy for securing capital for the company and marketing the product. He used to work almost 14-16 hours a day. He noticed that during sexual activities with his girl friend he could not control the ejaculation resulting in disappointment from his female partner. Because of the premature ejaculation problem he was trying to avoid sexual contact with his female partner whenever possible and his partner was feeling unfulfilled sexual experience and sometimes anger. The patient was provided with 500 mg capsules of formulation 4 in example 3 and advised to take 2 capsule approximately 3 hours before intercourse and 1 capsule approximately 1 hour before intercourse. He took 2 capsules in the first night and according to his testimony, he felt slightly numb in his penis and he was able to arouse his female partner's sexual feelings by performing pre-intercourse sexual conducts and his partner was able to perform pre-intercourse sexual conducts with his penis for almost half hour without any ejaculation. He was able to perform intercourse for more than 20 minutes and his partner felt exhaustion. His female partner was so ecstatic and he was able to perform sexual intercourse 2 times that night. The patient is periodically taking the capsules whenever he wants to have a good and sound sexual intercourse for his otherwise stressful body.

EXAMPLE 5

An Indian male, age 47, was involved in various businesses. He spent lot of his time in the business aspect and used to drink at dinner meetings to alleviate his stress due to his hectic business activities. Whenever he had tried to engage in romantic and sexual activities with his wife, he noticed that he could not hold his erection due to early ejaculation. His wife used to feel that she was not being loved by her husband and she used to feel abandoned by her husband. He used to feel embarrassed whenever he was with his wife and he sought help to alleviate his miserable sexual life. He was provided the pharmaceutical formulation of formulation 5 in example 3. During the first day he took 2 capsules 3-4 hours before his sexual activity and 1 capsule 1 hour before. He felt slight numbness around his penis and he felt very relaxed during his sexual act with his wife. He and his wife had intercourse for more than an hour and his wife said afterwards she never felt this happy during her entire life. Both were exhausted after the sexual act. Now whenever he needs satisfaction and comfort in his sex life, he takes the pharmaceutical composition described in this invention.

EXAMPLE 6

A white male of hispanic origin, born on Jun. 3, 1944 is working as a manager in a healthcare institution. He used to get up in the early morning and work late night attending various meetings. He has to bring quality patients to the hospital for treatment and has to find the proper physicians for taking care of these patients. He has to be on the phone for several hours a day and used to drink almost 4-5 cups of coffee a day. He used to feel exhausted and stressed out most of the day. At night he used to be awake thinking about his business activities and he noticed that whenever he is doing sexual act with his girlfriend he ejaculated within 1 minute of intercourse and his girlfriend used to be restless the entire night. He was asked to take two capsules of formulation 4 in example 3, 3-4 hours and 1 capsule 1 hour before doing sexual act. According to him, after taking the capsules and when he was engaged in sexual act he was very calm and confident and his girlfriend had played with his penis for nearly an hour without any discomfort. He had intercourse for more than 30 minutes and both were exhausted after the sexual conduct. According to him, his girlfriend was so ecstatic she didn't allow him to go to work the next day. Now he is constantly taking the capsules of whenever he needs a good and comfortable sexual conduct.

EXAMPLE 7

A white male of 39 yrs old who is living with his girl friend was keenly interested in the effect of the compositions of the present invention on his sexual activity. The subject consumed one (blue/yellow) capsule described as formulation 5 in example 3 at approximately 18:00. At 18:45 the subject reported a feeling of heaviness in the genitals with a slight feeling of flushing in the face. Sexual activity commenced at 19:15. Subject reported that his erection had a greater degree of stiffness and a sense of increased distension over that usually experienced. The subject reported that his staying power was increased by approximately 70% over his usual experience. Sexual intercourse was continued for approximately 90 minutes concluding with a more powerful than usual orgasm.

EXAMPLE 8

The Effect of Sildenafil, Dextromethorphan and Acetaminophen on CLASS II Males

In order to demonstrate the efficacy of Sildenafil and Dextromethorphan composition to treat premature ejaculation on CLASS II males, 22 volunteers have been chosen from the age groups of 28 and 57 who had premature ejaculation and erection problems. The volunteers were given capsules of formulation 4 in example 3. The volunteers were asked to take 2 capsules 2-3 hours before the sexual act and were asked to fill out a questionnaire form (as outlined below) before and after the sexual acts. The study was conducted for 8 weeks and the results were compiled and analyzed for sexual satisfaction. The results show that more than 80% of the volunteers were extremely satisfied with the composition of the invention for pre-mature ejaculation problems.

Sexual Function Study Home Questionnaire —Male

Please answer questions within 3-6 hours of taking capsule.
   Initials: _____
   Subject No.: _____
   Today's Date: _____
   Time: _____
   Date capsules Taken: _____
   Times: _____

The lines below represent the full range of feeling or response.

Please mark each line clearly with a vertical (straight up and down) stroke at the point which represents your response.

(There are no right or wrong answers. Do not write in boxes on right.)

1. What was your erection result after taking the capsules?
   No Rigid Erection [ ]
   Erection Suitable for Penetration [ ]
2. Did you have intercourse with wife/partner after taking tablet? [ ] Yes [ ] No IF NO please circle all reasons that apply:
   0—No erection. [ ]
   1—Erection not sufficient for penetration. [ ]

2—Felt sick after taking the capsules. [ ]
3—I decided not to participate in intercourse. [ ]
4—Wife/partner decided not to participate. [ ]
5—Unrelated interruption (example, telephone call). [ ]
6—Wife/partner menstruating. [ ]
7—Other, explain:

_____
_____ [ ]

3. What was your level of satisfaction with this attempt at sexual intercourse?
Extremely Satisfied [ ]
Extremely Unsatisfied:_____ [ ]
3. How long you were able to keep the erection before ejaculation with this attempt at sexual intercourse?
Erection Time Less than 3 Minutes [ ]
Erection Time 3-6 Minutes [ ]
Erection Time 6-10 Minutes [ ]
Erection Time More than 10 Minutes [ ]

4. Please describe any adverse reactions you experienced after taking, the capsules. (Indicate when the reaction started and stopped, and any intervention taken)

_____

_____

5. Other comments? _____

_____

The following references are incorporated in pertinent part by reference herein for all purposes.

REFERENCES

Albers, G. W., et al, "Safety and tolerance of oral dextromethorphan in patients at risk for brain ischemia," Stroke 22: 1075-1077 (1991).

Albers, G. W., et al, "Safety and tolerance of oral dextromethorphan in patients at risk for brain ischemia," Stroke 22: 1075-1077 (1991).

Applebaum, J. S., et al, "Dextromethorphan in the treatment of ALS: A pilot study," Abstract number 960S (page 393) in Neurology 41 (Suppl, 1), March 1991.

Applebaum, J. S., et al, "Dextromethorphan in the treatment of ALS: A pilot study," Abstract No. 960S (p. 393) in Neurology 41 (Suppl. 1), March 1991.

Balon (1996), "Antidepressants in the Treatment of Premature Ejaculation," Journal of Sex & Marital Therapy, 22(2):85-96.

Brinn, R., et al, "Sparteine oxidation is practically abolished in quinidine-treated patients," Br. J. Clin. Pharmacol. 22: 194-197 (1986).

Broly, F., et al, "Effect of quinidine on the dextromethorphan O-methylase activity of microsomal fractions from human liver," Br. J. Clin. Pharmacol. 28: 29-36 (1989).

Broly, F., et al, "Inhibitory studies of mexiletine and dextromethorphan oxidation in human liver microsomes," Biochem. Pharmacol. 39: 1045-1053 (1990).

Brosen, K., et al, "Extensive metabolizers of debrisoquin become poor metabolizers during quinidine treatment," Pharmacol. Toxicol. 60: 312-314 (1987)

Brosen, K., et al, "Extensive metabolizers of debrisoquin become poor metabolizers during quinidine treatment," Pharmacol. Toxicol. 60: 312-314 (1987).

Bruno Battistini, Regina Botting and Y. S. Bakhle, "COX-1 and COX-2: Toward the Development of More Selective NSAIDs" in Drug News and Perspectives, Vol. 7, pp. 501-512, 1994.

Carpenter, C. L., et al, "Dextromethorphan and dextrorphan as calcium channel antagonists," Brain Research 439: 372-375 (1988)

Cavallini (1995,) "Alpha-1 Blockade Pharmacotherapy in Primitive Psychogenic Premature Ejaculation Resistant to Psychotherapy," Eur. Urology 28:126-130.

Choi, D. W., "Dextrorphan and dextromethorphan attenuate glutamate neurotoxicity," Brain Res. 402: 333-336 (1987)

Craviso, G. L., and Musacchio, J. M., "High affinity dextromethorphan binding sites in guinea pig brain," Mol. Pharmacol. 23: 619-640 (1983).

David B. Reitz and Karen Seibert, "Selective Cyclooxygenase Inhibitors" in Annual Reports in Medicinal Chemistry, James A. Bristol, Editor, Vol. 30, pp. 179-188, 1995.

David J. Edwards, et al., "Identification of 6',7'-Dihydroxybergamottin, a Cytochrome P450 Inhibitor, In Grapefruit Juice", Drug Metabolisms and Disposition, vol. 24, No. 12, pp. 1287-1290, 1996.

Dayer, R., et al, "Dextromethorphan O-demethylation in liver microsomes . . . " Clin. Pharmacol. Ther. 45: 34-40 (1989)

Feeser et al, Neurosci. Letters 86: 340-345 (1988)

Di Silverio et al. (1996), "Effects Compares de l'Incision Cervico-Prostatique (ICP) et de l'Association ICP et Agonistes de la LHRH dans le Traitement de l'Hypertrophie Benigne de la Prostate," Journal D'Urologie 102(3): 11-116.

Don E. Griswold and Jerry L. Adams, "Constituative Cyclooxygenase (COX-1) and Inducible Cyclooxygenase (COX-2): Rationale for Selective Inhibition and Progress to Date" in Medicinal Research Reviews, Vol. 16, pp. 181-206, 1996.

Falaschi et al. (1981), "Brain Dopamine and Premature Ejaculation: Results of Treatment with Dopamine Antagonists," Apomorphine and Other Dopaminomitics 1:117-121.

Feinberg (1991), "Clomipramine for Obsessive-Compulsive Disorder," AFP Clinical Pharmacology 43(5): 1735-1738.

Ferkany et al, Eur. J. Pharmacol. 151: 151-154 (1988)

Ferrari et al (1994), "The Selective D2 Dopamine Receptor Antagonist Eticlopride Counteracts the Ejaculatio Praecox Induced by the Selective D2 Dopamine Agonist SND 919 in the Rat," Life Sciences 55(14):1155-1162.

Fonne-Pfister et al, Biochem. Biophys. Res. Communic. 148: 1144-1150 (1987)

Frank H. Bellevue, et al., "Synthesis and Biological Evaluation of 6',7'-Dihydroxybergamottin (6,7-DHB), A Naturally Occurring Inhibitor of Cytochrome P450 3A4", Biorganic & Medicinal Chemistry Letter, vol. 7, No. 20, pp. 2593-2598, 1997.

Guttendorf, R. J., et al., "Simplified phenotyping with dextromethorphan by thin-layer chromatography," Ther. Drug. Monit. 10: 490-498 (1988).

Hull et al. (1994), "The Roles of Nitric Oxide in Sexual Function of Male Rats," Neuropharmacology 33(11): 1499-1504.

Goldstein et al., "Oral Sildenafil in the Treatment of Erectile Dysfunction," The New England Journal of Medicine, 338, pp 1397-1404 (1998).

Inaba, T., et al, "In vitro inhibition studies of two isozymes of human liver cytochrome P-450," Drug Metabolism and Disposition 13: 443-447 (1985)

Inaba, T., et al, "Quinidine: Potent inhibition of sparteine and debrisoquin oxidation in vivo," Br. J. Clin. Pharmacol. 22: 199-200 (1986) Koppel, C., et al, "Urinary metabolism of dextromethorphan in man," Arzneim. Forsch./Drug Research 37: 1304-1306 (1987)

Inaba, T., et al, "Quinidine: Potent inhibition of sparteine and debrisoquin oxidation in vivo," Br. J. Clin. Pharmacol. 22: 199-200 (1986).

J. Rashid, et al., "Quercetin, an in vitro inhibitor of CYP3A, does not contribute to the interaction between nifedipine and grapefruit juice", Br J din Pharmac, vol.36, pp. 460-463, 1993.

M. R. Jachau, "Substrates, Specificities and Functions of the P450 Cytochromes", LIFE SCIENCES, Vol. 47, pp. 2385-2394(1990).

J. J. Neal, et al., "Inhibition of Insect Cytochromes P450 by Furanocoumarins", 1994, Pesticide Biochemistry and Physiology 50, pp. 43-50.

Jerzy Klinger (2000) "Vita Sexualis:The truth about human sex life", By Klinger, Pawel, Translated from Polish to English by Klinger, Jerzy, Copyright®1994 pages 1-362.

John Vane, "Towards a better aspirin" in Nature, Vol. 367, pp. 215-216, 1994.

Kan He, et al., "Inactivation of Cytochrome P450 3A4 by Bergamottin, a Component of Grapefruit Juice", Chem. Res. Toxicol, vol. 11, pp. 252-259, 1998.

Katsuyuki Fukuda, et al., "Grapefruit Component Interacting with Rat and Human P450 CYP3A: Possible Involvement of Non-Flavenoid Components in Drug Interaction", Biol. Pharm. Bull., vol. 20, No. 5, pp. 560-564, May 1997. Koppel, C., et al, "Urinary metabolism of dextromethorphan in man," Arzneim.-Forsch./Drug Research 37: 1304-1306 (1987).

Koyuncuoglu & Saydam, Intnl. J. Clin. Pharmacol. Ther. Tox. 28: 147-152 (1990)

Kupfer, A., et al "Dextromethorphan as a safe probe for debrisoquine hydroxylation polymorphism," Lancet ii: 517-518 (1984).

Leander, Epilepsy Res. 4: 28-33 (1989)

M. Bourian, et al., "Coumarin Derivatives in Grapefruit Juice and Their Interactions with Mammalian Drug Metabolising Enzyme Systems", Annual Congress on Medicinal Plant Research, vol. 44, pp. 43, 1996.

M. T. Obermeier, et al., "Effects of bioflavonoids on hepatic P450 activities", Xeonbiotica, vol. 25, No. 6, pp. 575-584, 1995.

Marina Tinel, et al., "Inactivation of Human Liver Cytochrome P-450 by the Drug Methoxsalen and Other Psoralen Derivatives", Biochemical Pharmacology, vol. 36, No. 6, pp. 951-955, 1987.

Metz et al. (1997), "Premature Ejaculation: A Psychophysiological Review," Journal of Sex & Marital Therapy 23(1):3-23.

Musacchio, J. M., et al, "High affinity dextromethorphan binding sites in the guinea pig brain," J. Pharmacol. Exp. Ther. 247: 424-431 (1988)

Napoli-Farris et al. (1984), "Stimulation of Dopamine Autoreceptors Elicits Premature Ejaculation in Rats," Pharmacology Biochemistry & Behavior 20:69-72.

Nielsen, M. D., et al, "A dose-effect study of the in vivo inhibitory effect of quinidine on sparteine oxidation in man," Br. J. Clin. Pharmacol. 29: 299-304 (1990).

Niznik et al, Arch. Biochem. Biophys. 26: 424-432 (1990)

Physician's Desk Reference, 44th Edition (1988), pp. 670-671 (Medical Economics Company, 1990).

Prince & Feeser, Neurosci. Letters 85: 291-296 (1988) quinidine-treated patients," Br. J. Clin. Pharmacol 22: 194-197 (1986)

Ramachander, G., et al, "Determination of dextrorphan in plasma and evaluation of bioavialability dextromethorphan hydrobromide in humans," J. Pharm. Sci 66: 1047-1048 (1977)

Rodd, E. H., Chemistry of Carbon Compounds (Elsevier Publ., New York, 1960).

Steinberg, G. K., et al, "Delayed treatment with dextromethorphan and dextrorphan reduces cerebral damage after transient focal ischemia," Neurosci Letters 89: 193-197 (1988).

B. Testa and P. Jenner, "Inhibitors Of Cytochrome P-450s and Their Mechanism of Action", DRUG METABOLISM REVIEWS, 12(1)1-117 (1981); F. P. Guengerich, "Cytochrome P450: Advances and Prospects", FASEB J., Vol. 6, pp. 667-668 (1992).

Tortella et al, TIPS 10: 501-507 (1989)

Uwe Fuhr, et al., "Inhibitory effect of grapefruit juice and its bitter principal, naringenin, on CYP1A2 dependent metabolism of caffeine in man*", Br. J. Clin. Pharmacol., Department of Clinical Pharmacology, University Hospital. Frankfurt/Main, Germany, vol. 35, 1993, pp 431-436.

Vettican, S. J., et al, "Phenotypic differences in dextromethorphan metabolism," Pharmaceut Res. 6: 13-19 (1989)

Waldinger et al. (1997), "Ejaculation-Retarding Properties of Paroxetine in Patients with Primary Premature Ejaculation: A Double-Blind, Randomized, Dose-Response Study," British Journal of Urology 79:592-595. (4 pages) 2 patents reference this [Article info]

Walker, E. O., and Hunt, V. P., "An open label trial of dextromethorphan in Huntington's Disease," Clin. Neuropharmacol. 12: 322-330 (1989).

William K. Chan, et al., "Mechanism-Based Inactivation of Human Cytochrome P450 3A4 by Grapepfruit Juice and Red Wine", Life Sciences, vol. 62, No. 10, pp. PL 135-142, 1998.

Wong, B. Y., et al, "Dextrorphan and dextromethorphan, common antitussives, are antiepileptic and antagonize NMDA in brain slices," Neurosci Letters 85: 21-26 (1988)

Yingna Cai, et al. "Inhibition and Inactivation of Murine Hepatic Ethoxy-and Pentoxyresorufin O-Delkylase by Naturally Ocurring Coumarins", Chem. Res. Toxicol, vol. 6, pp. 872-879, 1993.

K. Brosen; M. Murray and C. F. Reidy, "Recent Developments In Hepatic Drug Oxidation Implications For Clinical Pharmacokinetics", CLIN. PHARMACOKINET., 18(3): 220-239, 1990.

M. Murray and G. F. Reidy, "Selectivity in the Inhibition of Mammalian Cytochrome P-450 By Chemical Agents", PHARMACOLOGICAL REVIEWS, 42, 85-101 (1990).

T. D. Porter and M. J. Coon, "Cytochrome P-450: Multiplicity of Isoforms, Substrates, and Catalytic and Regulatory Mechanisms", J. BIOL. CHEM., Vol. 266, 13469-13472 (1991).

F. P. Guengerich, "Characterization of Human Microsomal Cytochrome P-450 Enzymes", ANNU. REV. PHARMACOL. TOXICOL. Vol, 29, pp. 241-264 (1989).

Martindale, The Extra Pharmacopoeia, 31 st edition, at p. 333 (London: The Royal Pharmaceutical Society, 1996).

Simmons et. al. "Nonsteroidal Anti-Inflammatory Drugs, Acetaminophen, Cyclooxygenase 2, and Fever". *Clinical Infectious Diseases.* 2000; 31 (Suppl 5):S211-8.

Botting, Regina M. "Mechanism of Action of Acetaminophen: Is there a Cyclooxygenase 3?". *Clinical Infectious Diseases.* 2000; 31 (Suppl 5):S202-10.

What is claimed is:

1. A method for delaying the onset of ejaculation in a male individual, comprising administering to the individual a pharmaceutical formulation consisting essentially of dextromethorphan, sildenafil, and acetaminophen in an amount effective to delay the onset of ejaculation by the individual during sexual intercourse, wherein said administration is oral, parenteral or by intracavernosal injection.

2. The method of claim 1, wherein said administration is parenteral.

3. The method of claim 1, wherein said administration is by intracavernosal injection.

4. A method for delaying the onset of ejaculation in a male individual who has a premature ejaculation problem, comprising administering to the individual a pharmaceutical formulation consisting essentially of a combination of sildenafil, dextromethorphan, and acetaminophen in an amount effective to delay the onset of ejaculation by the individual during sexual intercourse, wherein the formulation is administered orally, parenterally or by intracavernosal injection.

5. The method of claim 4, wherein the formulation is administered parenterally.

6. The method of claim 4, wherein the formulation is administered by intracavernosal injection.

7. The method of claim 4, wherein the sildenafil, dextromethorphan, and acetaminophen are administered combined in a single dosage form.

8. The method of claim 1, wherein the pharmaceutical formulation consists of dextromethorphan, sildenafil and acetaminophen in an amount effective to delay the onset of ejaculation by the individual during sexual intercourse, and a pharmaceutically acceptable carrier or excipient.

9. The method of claim 4, wherein the pharmaceutical formulation consists of dextromethorphan, sildenafil and acetaminophen in an amount effective to delay the onset of ejaculation by the individual during sexual intercourse, and a pharmaceutically acceptable carrier or excipient.

\* \* \* \* \*